United States Patent [19]

Brunner

[11] 4,139,633
[45] Feb. 13, 1979

[54] PHARMACEUTICAL PREPARATIONS FOR THE TREATMENT OF HYPERTONIA

[75] Inventor: Hellmut Brunner, Therwil, Switzerland

[73] Assignee: Ciba-Geigy Corporation, Ardsley, N.Y.

[21] Appl. No.: 661,892

[22] Filed: Feb. 27, 1976

Related U.S. Application Data

[63] Continuation-in-part of Ser. No. 512,747, Oct. 7, 1974, abandoned, which is a continuation of Ser. No. 260,681, Jun. 7, 1972, abandoned.

[30] Foreign Application Priority Data

Jun. 15, 1971 [CH] Switzerland ........................ 8705/71

[51] Int. Cl.² ................... A61K 31/40; A61K 31/135

[52] U.S. Cl. ...................................... 424/274; 424/330
[58] Field of Search ................................ 424/274, 330

[56] References Cited

PUBLICATIONS

Boehringer et al.–Chem. Abst., vol. 75 (1971), p. 129, 559S.

Richardson et al.–Circulation, vol. 37 (Apr. 1968), pp. 534–542.

*Primary Examiner*—Sam Rosen
*Attorney, Agent, or Firm*—John J. Maitner

[57] ABSTRACT

The present invention relates to new pharmaceutical preparations comprising a β-receptor blocking agent and a diuretic, processes for their preparation and the use of said preparations for the treatment of hypertonia.

7 Claims, No Drawings

NEW PHARMACEUTICAL PREPARATIONS FOR THE TREATMENT OF HYPERTONIA

This is a continuation-in-part of our copending application Ser. No. 512,747 filed Oct. 7, 1974 now abandoned which in turn is a continuation of our copending application Ser. No. 260,681 filed June 7, 1972 now abandoned.

The invention relates to new pharmaceutical preparations for the treatment of hypertonia, which are distinguished relative to the prior therapy predominantly through the absence of side-effects.

In the hitherto customary therapy of arterial hypertension substances were used which in a high percentage of the cases led to sedation (for example in the case of reserpin, methyldopa or clonidine), to orthostatic disturbances of the blood-pressure (for example in the case of guanethidine, bethanidine and related substances) or to hypercirculation and tachycardia (for example hydralazines or guancydines). These disturbances are in each case related to the mechanism of action of the substances, which explains the great frequency of the occurrence of side-effects. In addition, these are not the sole side-effects of the particular preparations.

An arterial hypertonia can be adequately controlled in about 40% of the cases by an adrenergic beta-receptor blocking agent (for example 1-(2-allyloxyphenoxy)-2-hydroxy-3-isopropylaminopropane hydrochloride) in daily doses of 120–480 mg. Diuretics alone (for example hydrochlorothiazide in a daily dose of 20–60 mg) are also able favourably to influence the blood-pressure in about 30–40% of the patients.

It has now been found that through the combined administration of specific members of both types of active substances the probability of therapeutic success can be substantially increased, since the actions of the two combined types of active substances supplement one another in a surprising fashion in such a way that it corresponds to at least an addition of the individual actions.

This creates an anti-hypertensive agent which is outstandingly suitable for practical purposes and which does not cause any of the side-effects mentioned (sedation, orthostatic disturbances or hypercirculation). Since sedation, orthostasis or hypercirculation interfere with the customary life and capacity for work (for example car driving) of the patients, the new preparations represent an unmistakable considerable advance in the therapy of hypertonia.

The invention therefore relates to pharmaceutical preparations which contain a β-blocking agent selected from 1-(2-allyloxyphenoxy)-2-hydroxy-3-isopropylaminopropane, and 1-[4-(2-methoxyethyl)-phenoxy]-2-hydroxy-3-isopropylaminopropane and non-toxic salts thereof, together with a diuretic selected from 2-chloro-5-(1-hydroxy-3-oxo-1-isoindolyl)-benzenesulphonamide (1-oxo-3-(3-sulphamyl-4-chlorophenyl)-3-hydroxyisoindoline) or 6-chloro-7-sulphamyl-3,4-dihydro-1,2,4-benzothiadiazine-1,1-dioxide, and 3-cyclopentylmethyl-6-chloro-7-sulphamyl-3,4-dihydro-1,2,4-benzothiadiazine-1,1-dioxide, and to the manufacture of these preparations, as well as to the use of these, for the treatment of hypertonia.

By virtue of their asymmetric carbon atom, the β-blocking agents which have been mentioned can be in the form of racemates or optical antipodes. Preferably, they are used in the form of their racemate or of the more active or less toxic antipode.

The β-blocking agents mentioned can furthermore be in the free from or in the form of their non-toxic salts. Possible salts of this nature are especially salts with organic or inorganic acids, such as, for example: hydrogen halide acids, sulphuric acids, phosphoric acids, nitric acid, perchloric acid, aliphatic, alicyclic, aromatic or heterocyclic carboxylic or sulphonic acids, such as formic, acetic, propionic, succinic, glycollic, lactic, malic, tartaric, citric, ascorbic, maleic, hydroxymaleic or pyruvic acid; phenylacetic, benzoic, p-aminobenzoic, anthranilic, p-hydroxybenzoic, salicyclic or p-aminosalicylic acid, embonic acid, methanesulphonic, ethanesulphonic, hydroxyethanesulphonic and ethylenesulphonic acid; halogenobenzenesulphonic, toluenesulphonic and naphthalenesulphonic acid or sulphanilic acid; cyclohexyl-sulphamic acid, methionine, tryptophane, lysine or arginine.

In the new preparations, the ratio of β-blocking agent to diuretic can be varied within wide limits.

The dosage of the new preparations naturally depends on the activity of the particular β-blocking agents and diuretics and on the individual requirements of the patient. For the β-blocking component it can, for example, lie between half and twice the separate dose, with half to one separte dose being used preferentially. Thus, for example, the abovementioned parcularly preferred preparations can contain 20 to 160 mg, especially 40 to 80 mg. of 1-(2-allyloxyphenoxy)-2-hydroxy-3-isopropylaminopropane or of a non-toxic salt thereof, e.g. the hydrochloride or 20 to 160 mg, especially 40 to 100 mg, of 1-[4-(2-methoxyethyl)-phenoxy]-2-hydroxy-3-isopropylaminopropane or of a non-toxic salt thereof, e.g. the (2:1)-tartrate. The dosage of the diuretic can lie between half and twice the separate dose, with half to one separate dose being used preferentially. Thus, for example, the above-mentioned preferred preparations can contain 10 to 25 mg, especially 10 mg, 12,5 mg or 25 mg of 2-chloro-5-(1-hydroxy-3-oxo-1-isoindolinyl)-benzenesulphonamide or 10 to 25 mg, especially 10 mg, of 6-chloro-7-sulphamyl-3,4-dihydro-1,2,4-benzothiadiazine-1,1-dioxide or 0,1 to 0,5 mg, especially 0,25 mg of 3-cyclopentylmethyl-6-chloro-7-sulphamyl-3,4-dihydro-1,2,4-benzothiadiazine-1,1-dioxide.

The new pharmaceutical preparations are principally suitable for oral administration and can, as such, contain the customary excipients, such as, for example, lactose, starch, gelatine, colloidal silica, magnesium stearate, talc, phenylvinylpyrrolidone and the like. Furthermore, they can also contain yet further therapeutically valuable substances as an admixture. They are in the form of, for example, tablets, dragees or capsules. They are obtained in the customary manner. For rectal administration, the new pharmaceutical preparations are in particular in the form of suppositories which are obtained in the customary manner.

The preparations according to the invention, especially those mentioned preferentially, can advantageously contain potassium chloride, and preferably 200 to 800 mg, especially 500 to 700 mg, are used per dosage unit (capsule).

the diuretics and β-blocking agents used are known and/or can be manufactured in a known manner.

The invention is described in the examples which follow without intending thereby to restrict its scope in any way.

EXAMPLE 1

Tablets containing 40 mg of 1-(2-allyloxyphenoxy)-2-hydroxy-3-isopropylamino-propane hydrochloride and 10 mg of 6-chloro-7-sulphamyl-3,4-dihydro-1,2,4-benzothiadiazine-1,1-dioxide.

| Composition | |
|---|---|
| 1-(2-Allyloxyphenoxy)-2-hydroxy-3-isopropylamino-propane hydrochloride | 40 mg |
| 6-Chloro-7-sulphamyl-3,4-dihydroxy-1,2,4-benzothiadiazine-1,1-dioxide | 10 mg |
| Lactose | 123 mg |
| Wheat starch | 90 mg |
| Colloidal silica | 10 mg |
| Polyvinylpyrrolidone | 10 mg |
| Talc | 15 mg |
| Magnesium stearate | 2 mg |
| | 300 mg |

Manufacture

The two active substances are mixed with the lactose, the colloidal silica and a part of the wheat starch. The mixture if forced through a sieve and kneaded with an aqueousalcoholic solution of polyvinylpyrrolidone until a plastic mass has been produced. This is forced through a sieve and dried, and the dry granules are again sieved. Thereafter the residual wheat starch, talc and magnesium stearate are mixed in and the mixture is pressed into tablets weighing 300 mg and having a breaking groove.

EXAMPLE 2

Dragées containing 40 mg of 1-(2-allyloxyphenoxy)-2-hydroxy-3-isopropylamino-propane hydrochloride, 10 mg of 6-chloro-7-sulphamyl-3,4-dihydro-1,2,4-benzothiadiazine-1,1-dioxide and 600 mg of potassium chloride.

| Composition | |
|---|---|
| Core | |
| Potassium chloride | 600 mg |
| Stearyl alcohol | 77 mg |
| Polyvinylpyrrolidone | 20 mg |
| Magnesium stearate | 3 mg |
| | 700 mg |
| Protective lacquer | 20 mg |
| Covering | |
| 1-(2-Allyloxyphenoxy)-2-hydroxy-3-isopropylamino-propane hydrochloride | 40 mg |
| 6-Chloro-7-sulphamyl-3,4-dihydro-1,2,4-benzothiadiazine-1,1-dioxide | 10 mg |
| Sugar, talc, dyestuff, and binders q.s. ad | 280 mg |
| | 1000 mg |

MANUFACTURE

The potassium chloride is granulated with the stearyl alcohol melt and a concentrated polyvinylpyrrolidone solution, and the mixture is dried. The resulting mass is sieved and pressed in to blanks weighing 700 mg. These are coated with a layer of protective lacquer and then dragée-coated with dyed sugar syrup in which the two active substances are dissolved or suspended, to give a final weight of approx. 1 g.

EXAMPLE 3

Tablets containing 20 mg of 1-1-(2-allyloxyphenoxy)-2-hydroxy-3-isopropylamino-propane hydrochloride and 10 mg of 2-chloro-5-(1-hydroxy-3-oxo-1-isoindolinyl)-benzenesulphonamide.

| Composition | |
|---|---|
| 1-1-(2-Allyloxyphenoxy)-2-hydroxy-3-isopropylamino-propane hydrochloride | 20 mg |
| 2-Chloro-5-(1-hydroxy-3-oxo-1-isoindolinyl)-benzenesulphonamide | 10 mg |
| Lactose | 57 mg |
| Wheat starch | 45 mg |
| Colloidal silica | 5 mg |
| Polyvinylpyrrolidone | 5 mg |
| Talc | 7 mg |
| Magnesium stearate | 1 mg |
| | 150 mg |

MANUFACTURE

The two active substances are mixed with the lactose, the colloidal silica and a part of the wheat starch. The mixture is forced through a sieve and kneaded with an aqueousalcoholic solution of polyvinylpyrrolidone until a plastic mass has been produced. This is forced through a sieve and dried, and the dry granules are again sieved. Thereafter the remaining wheat starch, talc and magnesium stearate are mixed in and the mixture is pressed into tablets weighing 150 mg and having a breaking groove.

EXAMPLE 4

Tablets containing 80 mg of 1-(2-allyloxyphenoxy)-2-hydroxy-3-isopropylamino-propane hydrochloride and 10 mg of 2-chloro-5-(1-hydroxy-3-oxo-1-isoindolinyl)-benzenesulphonamide.

| Composition | |
|---|---|
| 1-(2-allyloxyphenoxy)-2-hydroxy-3-isopropylamino-propane hydrochloride | 80 mg |
| 2-chloro-5-(1-hydroxy-3-oxo-1-isoindolinyl)-benzenesulphonamide. | 10 mg |
| lactose | 94 mg |
| maize starch | 41 mg |
| methylcellulose | 8 mg |
| colloidal silica | 5 mg |
| talc | 9 mg |
| magnesium stearate | 3 mg |
| | 250 mg |

Manufacture

The two active substances 1-(2-allyloxyphenoxy-)-2-hydroxy-3-isopropylamino-propane hydrochloride and 2-chloro-5-(1-hydroxy-3-oxo-1-isoindolinyl)-benzenesulphonamide are mixed with the lactose, colloidal silica, a part of the maize starch and the methylcellulose. The mass is compacted. The slugs are broken under addition of the residual maize starch, talc and magnesium stearate. After mixing the granulate is compressed into tablets weighing 250 mg.

EXAMPLE 5

Tablets containing 160 mg of 1-(2-allyloxyphenoxy)-2-hydroxy-3-isopropylamino-propane hydrochloride and 0.25 mg of 3-cyclopentylmethyl-6-chloro-7-sulphamoyl-3,4-dihydro-1,2,4-benzothiadiazine-1,1-dioxide

| Composition | |
|---|---|
| 1-(2-allyloxyphenoxy)-2-hydroxy-3-isopropylamino-propane hydrochloride | 160 mg |
| 3-cyclopentyl-6-chloro-7-sulphamoyl-3,4-dihydro-1,2,4-benzothiadiazine-1,1-dioxide | 0,25 mg |

| Composition | |
|---|---|
| lactose | 120 mg |
| microcrystalline Cellulose | 62 mg |
| polyvinylpyrrolidone | 8 mg |
| talc | 20 mg |
| magnesiumstearate | 10,75 mg |
| Magnesiumstearate | 4 mg |

Manufacture 3-cyclopentyl-6-chloro-7-sulphamoyl-3,4-dihydro-1,2,4-benzothiadiazine-1,1-dioxide is premixed with a part of lactose. The mixture is added to 1-(2-allyloxyphenoxy)-2-hydroxy-3-isopropylamino-propane hydrochloride, the residual lactose a part of microcrystalline cellulose, colloidal silica and granulated with an aqueous solution of polyvinylpyrrolidone. The plastic mass is forced through a sieve, dried and sieved again under addition of the residual microcrystalline cellulose, talc and magnesiumstearate. After the final mixing the granulate is compressed into tablets weighing 385 mg.

EXAMPLE 6

| Composition | |
|---|---|
| 1-[4-(2-methoxyethyl)-phenoxy]-2-hydroxy-3-isopropyl-amino-propane-(2:1) tartrate | 100,0 mg |
| 2-chloro-5-(1-hydroxy-3-oxo-1-isoindolinyl-benzenesulphonamide | 12,5 mg |
| colloidal silica | 8,5 mg |
| microcrystalline cellulose | 60,0 mg |
| magnesiumstearate | 2,0 mg |
| maize starch | 20,0 mg |
| polyvinylpyrrolidone | 7,0 mg |

Manufacture

To produce 20,000 capsules having an active-substance content of 100 mg of 1-[4-(2-methoxyethyl)-phenoxy]-2-hydroxy-3-isopropylamino-propane-(2:1) tartrate and 12.5 mg of 2-chloro-5-(1-hydroxy-3-oxo-1-isoindolinylbenzenesulphonamide per capsule, 2 kg of 1-[4-(2-methoxyethyl)-phenoxy]-2-hydroxy-3-isopropylamino-propane-(2:1) tartrate with 250 mg of 2-chloro-5-(1-hydroxy-3-oxo-1-isoindolinyl-benzenesulphonamide, 150 g of colloidal silica and 700 g of microcrystalline cellulose are put through a sieve having a mesh size of 1.6 mm; the sieved material is then granulated with an aqueous solution of 140 g of polyvinylpyrrolidone in a fluidised bed, and the granulated material is subsequently dried at 40° C. This granulate is then put through a sieve having a mesh size of 1.2 mm; the sieved material is mixed with 20 g of aerosil 200, 400 g of maize starch, 500 g of microcrystalline cellulose and 40 g of magnesium stearate, and the mixture is mechanically filled into 20,000 capsules, size 2.

EXAMPLE 7

| Composition | |
|---|---|
| 1-[4-(2-methoxyethyl)-phenoxy]-2-hydroxy-3-isopropyl-amino-propane-(2:1) tartrate | 100,0 mg |
| 2-chloro-5-(1-hydroxy-3-oxo-1-isoindolinyl)-benzene-sulphonamide | 25,0 mg |
| colloidal silica | 8,5 mg |
| microcrystalline cellulose | 57,5 mg |
| magnesium stearate | 2,0 mg |
| maize starch | 20,0 mg |
| polyvinylpyrrolidone | 7,0 mg |
| | 120,0 mg |

Manufacture

To produce 20,000 capsules having an active-substance content of 100 mg of 1-[4-(-methoxyethyl-phenoxy)-2-hydroxy-3-isopropylamino-propane-(2:1) tartrate and 250 mg of 2-chloro-5-(1-hydroxy-3-oxo-1-isoindolinyl)-benzenesulphonamide per capsule, 2 kg of 1-[4-(2-methoxyethyl)-phenoxy]-2-hydroxy-3-isopropylamino-propane-(2:1) tartrate with 500 g of 2-chloro-5-(1-hydroxy-3-oxo-1-isoindolinyl)-benzenesulphonamide, 150 g of colloidal silica and 700 g of microcrystalline cellulose are put through a sieve having a mesh size of 1.6 mm; the sieved material is then granulated with an aqeous solution of 140 g of polyvinylpyrrolidone in a fluidised bed, and the granulated material is subsequently dried at 40° C. This granulate is then put through a sieve having a mesh size of 1.2 mm; the sieved material is mixed with 20 g of aerosil 200, 400 g of maize starch, 450 g of microcrystalline cellulose and 40 g of magnesium stearate, and the mixture is mechanically filled into 20,000 capsules, size 2.

What I claim is:

1. A pharmaceutical preparation with anti-hypertensive properties comprising an amount of 20 mg to 160 mg of a beta-blocking agent selected from the group consisting of 1-(2-allyloxyphenoxy)-2-hydroxy-3-isopropylaminopropane or 1-[4-(2-methoxyethyl)-phenoxy]-2-hydroxy-3-isopropylaminopropane in the free form or in the form of its non-toxic salts and an amount of 10 mg to 25 mg of 2-chloro-5-(1-hydroxy-3-oxo-1-ioindolinyl)-benzene-sulphonamide.

2. Pharmaceutical preparation according to claim 1, containing 80 mg of 1-(2-allyloxyphenoxy)-2-hydroxy-3-isopropylaminopropane hydrochloride and 10 mg of 2-chloro-5-[1-hydroxy-3-oxo-1-isoindolinyl]-benzenesulphonamide.

3. Pharmaceutical preparation according to claim 1, containing 100 mg of 1-[4-(2-methoxyethyl)-phenoxy]-2-hydroxy-3-isopropylaminopropane-(2:1) tartrate and 25 mg of 2-chloro-5-(1-hydroxy-3-oxo-1-isoindolinyl)-benzenesulphonamide.

4. Pharmaceutical preparation according to claim 1, containing 100 mg of 1-[4-(2-methoxyethyl)-phenoxy]-2-hydroxy-3-isopropylaminopropane-(2:1) tartrate and 12,5 mg of 2-chloro-5-(1-hydroxy-3-oxo-1-isoindolinyl)-benzenesulphonamide.

5. Pharmaceutical preparation according to claim 1, containing potassium chloride.

6. Pharmaceutical preparation according to claim 1, containing 200 to 800 mg of potassium chloride.

7. Method for the treatment of hypertonia, characterised in that a pharmaceutical preparation according to claim 1 is administered to a warm-blooded organism in need of treatment.

* * * * *